(12) United States Patent
Stockel

(10) Patent No.: US 6,214,995 B1
(45) Date of Patent: Apr. 10, 2001

(54) REACTIVE HINDERED AMINE LIGHT STABILIZERS

(75) Inventor: Richard F. Stockel, 475 Rolling Hills Rd., Bridgewater, NJ (US) 08807

(73) Assignee: Richard F. Stockel, Bridgewater, NJ (US)

(*) Notice: Subject to any disclaimer, the term of this patent is extended or adjusted under 35 U.S.C. 154(b) by 0 days.

(21) Appl. No.: 09/218,647

(22) Filed: Dec. 22, 1998

(51) Int. Cl.⁷ .................................................. C07D 215/00
(52) U.S. Cl. ............................................ 546/16; 524/102
(58) Field of Search ............................. 546/16; 524/102

(56) References Cited

U.S. PATENT DOCUMENTS

| | | | |
|---|---|---|---|
| 3,536,722 | * 10/1970 | Murayama et al. | 260/294 |
| 3,941,744 | * 3/1976 | Murayama et al. | 260/45.8 N |
| 3,975,462 | * 8/1976 | Murayama et al. | 260/880 R |
| 4,162,246 | * 7/1979 | Soma et al. | 260/45.8 NT |
| 4,219,465 | * 8/1980 | Soma et al. | 260/45.8 NT |
| 4,233,410 | * 11/1980 | Rody et al. | 525/123 |
| 4,495,325 | * 1/1985 | DeBergalis et al. | 524/507 |
| 5,204,422 | * 4/1993 | Seltzer et al. | 526/204 |

OTHER PUBLICATIONS

Dagonneau, M. et al 'Chemistry of Hindered Amines From the Piperidine Series' Synthesis, pp. 895–916, Nov. 1984.*
Dagonneau, M. et al 'Sterically Hindered Amines and Nitroxyls as Polymer Stabilizers' Rev. Macromol. Chem. Phys C22(2), pp. 169–202, 1983.*

* cited by examiner

*Primary Examiner*—Amelia Owens

(57) ABSTRACT

This invention relates to new and novel compositions and processes, whereby hindered amine light stabilizers (HALS) having either one or more amido or imido groups and/or a phenolic or anilino group are reacted with an aldehyde to give hydroxy, alkylated groups. These hydroxyalkylated groups can be further reacted with lower alkyl alcohol's to give the more stable alkoxylated derivatives. The above compositions can then be used as reactive HALS for the following polymeric systems, e.g., aminoplasts epoxies, polyesters, polyamides, and urethanes and others to confer photo stabilization.

9 Claims, No Drawings

REACTIVE HINDERED AMINE LIGHT STABILIZERS

FIELD OF INVENTION

The present invention relates to compositions of reactive hindered amine light stabilizers, when added to certain polymers produced ultra-violet light stabilized materials. These photo-stabilizers are hindered amine light stabilizers (HALS) having one or more imido and/or amido functionalities which can be subsequently reacted with aldehydes, e.g., formaldehyde, to give hydroxyalkylated derivatives. The corresponding hydroxyalkylated compounds can be further reacted with lower alkyl alcohol's to give the more stable alkoxylated derivatives.

HALS containing an anilino or phenolic group, whereby the ortho and/or para positions are unsubstituted can be hydroxyalkylated and subsequently alkoxylated to confer desirable photo-stabilization properties to various polymers represent another class of ultra-violet absorbers of this invention.

HALS for the purpose of this invention has the following definition: A sterically hindered secondary amine with no alpha hydrogen atoms attached to the two carbons adjacent to the secondary amine nitrogen atom. Furthermore, the secondary amine nitrogen atom can be substituted by hydrogen, hydroxyl, ether, ester, amide, alkyl, aryl, and alkylaryl and the like.

DESCRIPTION OF THE PRIOR ART

It is know in this art that organic polymers used in the coatings, molding and laminating industries are degraded when they are subjected to extraneous agents, especially the combined action of air and ultra-violet radiation in sunlight. Such degradation is typically restricted by introducing small amounts of stabilizers into the polymer.

At present, some of the most effective of these UV stabilizers are the sterically hindered amines, in particular 2,2,6,6-tetramethylpiperidines. However, other none piperidyl HALS can also be employed in this investment.

In practice however, one of the major problems in the use of these stabilizers is to provide a good compromise between their effectiveness and the persistence of their activity, which employs the use of molecules of high molecular weight, which do not bloom.

SUMMARY OF THE INVENTION

Accordingly a major object of the present invention is the provision of novel reactive stabilizers, which conspicuously ameliorate these disadvantages and drawbacks to-date, characterizing the state of the art.

This invention involves novel compositions of matter comprising HALS, which are either hydroxyalkylated or an alkoxylated (lower alkyl group) thereof. The HALS having at least one imido and/or amido group, or preferably two or more of these groups, capable of being reacted with and aldehydes to give a hydroxyalkylated derivative and subsequently being capable of an alkoxylation with a lower alkyl alcohol. The reactivity of these HALS are the imido group

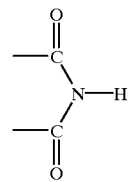

and/or the amido group when can be methylated with formaldehyde or other aldhydes

This can be further reacted with methanol, butanol, etc., to give a more stabile and more solvent soluble reactive product via etherification.

Furthermore, HALS containing either phenolic or anilino moieties can also be reacted with aldehydes e.g., formaldehyde and further reacted with a lower alkyl alcohol to form an alkoxylated derivative if desired, are additional effective reactive ultra-violet absorbers.

These type HALS can be copolymerized/co-reacted from about 1 to about 10 wt % with aminoplasts, epoxies, urethanes, polyamides, polyesters and other polymeric compositions having reactive functionalities like oxirane, amino, hydroxyl, thiol, anhydride and carboxyl groups. This invention is also a curable composition containing the novel stabilizers of this invention. This invention is also an improved method of stabilizing polymers wherein the improvement comprises adding to said polymers the novel stabilizers of this invention.

The advantages of the anchored stabilizers of this invention over their unanchored precursors include generally higher compatibility with polymers and resins and generally lower volatility due to high molecular weights.

DETAILED DESCRIPTION OF THE INVENTION

The novel HALS useful for this invention can be quite diversified in their chemical structure. However, they all must contain at least one or more amido and/or imido functional group. Another chemical moiety that is applicable for this invention involves the presence of an anilino and/or phenolic functionately within the HALs structure. Obviously, both of these functionalities can coexist is the same molecule.

HAL Structures

The following HALS are examples of structures which can be easily converted to useful chemically reactive HALS as illustrations for this invention. It is obvious that many other theoretical chemical structures can exit. Anyone skilled in the art of organic synthesis can conjure up other examples. Nevertheless, in order to be operative in this invention a sterically hindered amine having either one or more of a) imido and /or amido functionality, and/or b) phenolic or anilino functionality with one or more free ortho and/or para positions to introduce one or more hydroxyalkylated and/or alkoxylated groups.

Some Proposed Reactive HALS

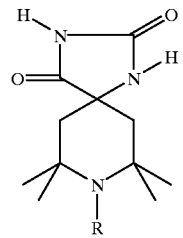

I

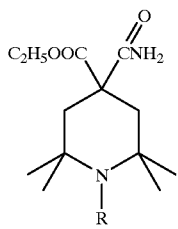

II

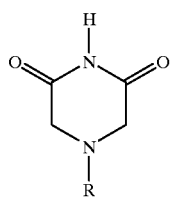

III

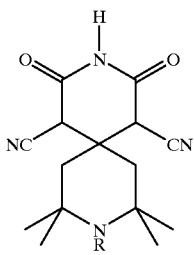

IV

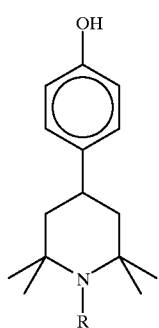

V

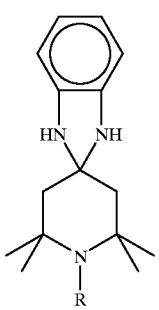

VI

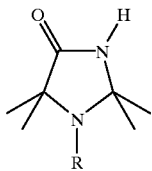

VII

The above structures (I–VII) are made reactive by forming hydroxyalkylated or alkoxylated derivatives thereof.

The preparation of all of these HALS (I–VII) prior to hydroalkylation or alkoxylation can be found in two publications; a) M. Dagonneau et. al., Rev. Macromol. Chem. Phys. C22 C21, p169–202 (1982–83), and b) M. Dagonneau et al, Synthesis, November 1984, p895–916.

It is to be understood that the foregoing examples are illustrative only and that other means and techniques can be employed without departing from the true scope of the invention as defined in the claims of this invention.

The following example serves to illustrate the invention.

EXAMPLE

Preparation of spiro (hydantoin-5,4'(tetramethyl-2', 2', 6', 6'- piperdine) (I) is prepared in 92% yield by reacting triacetoneamine with ammonium carbonate and sodium cyanide (Bucher - Bergs reaction) in alcohol and water. The synthesis is reported in Bull. Soc. Chim. p816, 1967, A. Rassat and Paul Rey.

Although the patent search revealed that Sankyo Company of Japan has a number of patents describing the synthesis of many spiro hydantoin piperidyl HALS, none of these patents described the hydroxyalkylation and alkoxylation reactions to form reactive ultra-violet absorbers. The patents related to the spirohydantoin piperidyl HALS are U.S. Pat. Nos. 3,536,722; 3,941,744; 3,975,462; 4,162,246; and 4,219,465, and are hereby incorporated into the body of this specification as precursors to some of the compositions of this invention.

Formation of Methylolated Melamine—Spirohydantoin HALS (I) Adduct

To a one neck 200 ml round bottom flask was added:

17.95 g melamine (0.143 moles)

1.68 g (I) (0.0075 moles)

97.5 g of a 37 wt. % formaldehyde solution

Adjust pH to 7.5 with sodium carbonate. Stir and heat to about 100° C. and maintain for 15–30 minutes, while the solution becomes clear. Continue these reaction conditions for one (1) hour, then cool to room temperature. Collect the white crystals, wash with ethanol, and dry keeping temperature below 40° C.

The product is an adduct of methylolated melamine and methylolated spirohydantoin HALS (I)—95/5 wt. % ratio. Both the FTIR and $^1$Hnmr are consistent with the proposed structure.

Structures II through VII can be reacted similarly with formaldehyde or other aldehydes and subsequently etherified, if desired. The resulting compositions can than be utilized as reactive HALS for aminoplasts, epoxies, polyamides, polyesters, urethanes and other suitable polymeric systems.

Aminoplasts constitute a very broad variety of compositions including melamine, urea thiourea, phenolic, sulfonamide, anilino, hydantoin, cyclic urone, cyanamide, dicyanodiamide, carbamates, glyoxal, acrylamide, polyacrylamide and benzoguanamine and others known in the prior art as being applicable for this invention.

When structures I through VII are hydroxyalkylated and/or etherified the resulting compositions can be useful for a variety of applications, e.g., molding materials, plastics, coatings, adhesives, paper and textile finishes and many other uses when reacted with such polymer systems as aminoplasts, alkyds, acrylics, esters, amides, epoxies, and urethanes. Permanent uv protection will be ascertained.

What is claimed:

1. A synthetic polymer composition stabilized against photo and thermal deterioration wherein there is incorporated, in a sufficient amount to prevent said deterioration, a compound having the formula I

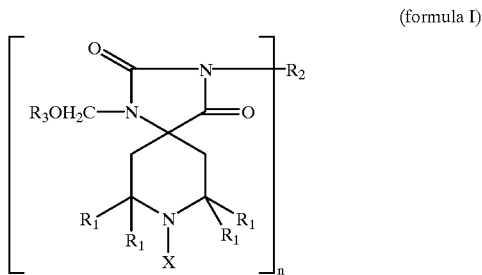

(formula I)

Wherein

X=hydrogen, alkyl, aryl, alkyl ether, aryl ether, alkyl ester, aryl ester, alkyl amide, aryl amide $R_1$=methyl $R_2$=hydroxymethylol, alkoxyalkyl, alkyl, ethoxylate, ethyl ester, ethyl amide where n=1, and alkylene or phenylene where n=2.

2. A compound as claimed in claim 1, wherein one or both nitrogen atoms of the hydantoin ring is a hydroxymethylolated derivative.

3. A compound as claimed in claim 1, wherein one or both nitrogen atoms of the hydantoin ring is an alkoxyalkyl derivative.

4. A composition comprising a synthetic polymer and a derivative of claim 1, wherein the latter is about 0.01 to about 5.0 weight percent based on the weight of the polymer.

5. A synthetic polymer composition wherein the polymer undergoes a reaction with compounds of claim 1 to achieve permanence by forming cross-linking networks.

6. A synthetic polymer composition wherein the polymer in non-reactive with compounds of claim 1, nevertheless permanence is achieved by self-cross-linking of claim 1 compounds.

7. The hydroxymethylolated or methoxylated hydroxymethylolated structure I.

8. The compositions of claim 1 whereby the aldehyde can be formaldehyde or furfuryl to give the corresponding hydroxyalkylated derivatives.

9. The compositions of claim 1 whereby the alkoxylation of the hydroxyalkylates is produced by using methanol, ethanol, n-propanol, 2-propanol, n-butanol, 2-butanol or t-butanol.

* * * * *